United States Patent [19]

Lescrenier

[11] 4,337,502

[45] Jun. 29, 1982

[54] LIGHT BEAM PRODUCING DEVICE

[76] Inventor: Charles Lescrenier, 660 Crescent Ct., Wauwatosa, Wis. 53213

[21] Appl. No.: 155,052

[22] Filed: Jun. 2, 1980

[51] Int. Cl.³ .............................................. F21V 7/04
[52] U.S. Cl. ..................................... 362/32; 362/259; 362/268; 362/308; 362/804; 250/491; 250/445 T
[58] Field of Search ................. 362/32, 259, 268, 804, 362/308; 250/491, 445 T

[56] References Cited

U.S. PATENT DOCUMENTS 4,011,403 3/1977 Epstein ................................ 362/32
4,206,494 6/1980 Lovering ............................. 362/32

Primary Examiner—Stephen J. Lechert, Jr.
Attorney, Agent, or Firm—Andrus, Sceales, Starke & Sawall

[57] ABSTRACT

A device for producing at least one beam of light having a desired configuration includes a source (12) of concentrated light. A fiber optic conductor (18) transmits the concentrated light to one or more locations remote from the source. Light beam forming means (22) receive the light from the fiber optic conductor (18) and form same into one or more beams of light having the desired configurations, such as a plane.

18 Claims, 5 Drawing Figures

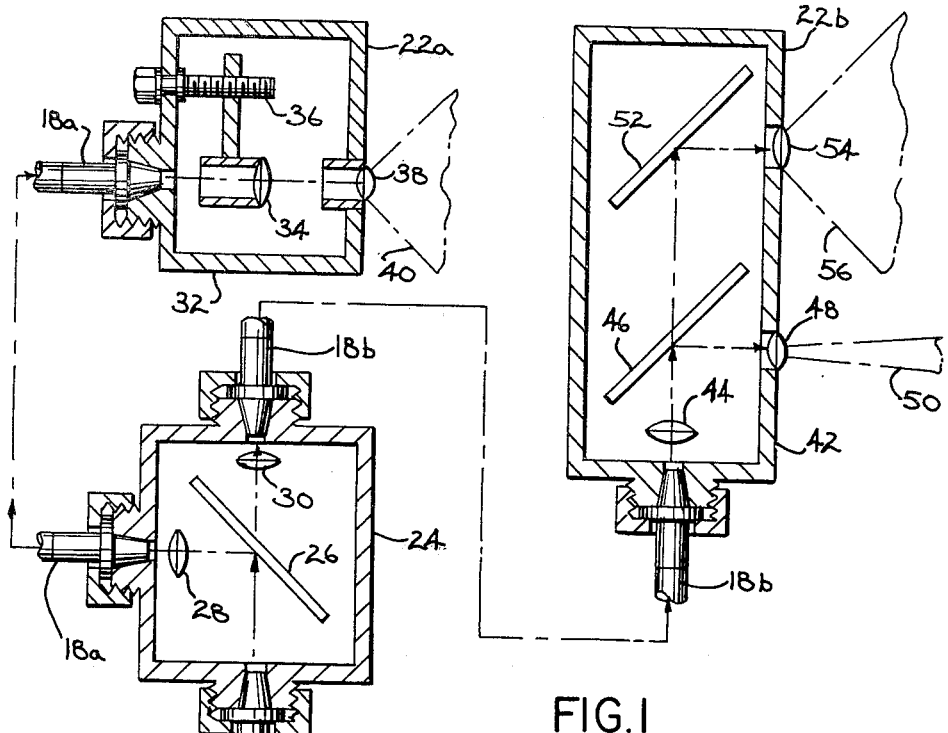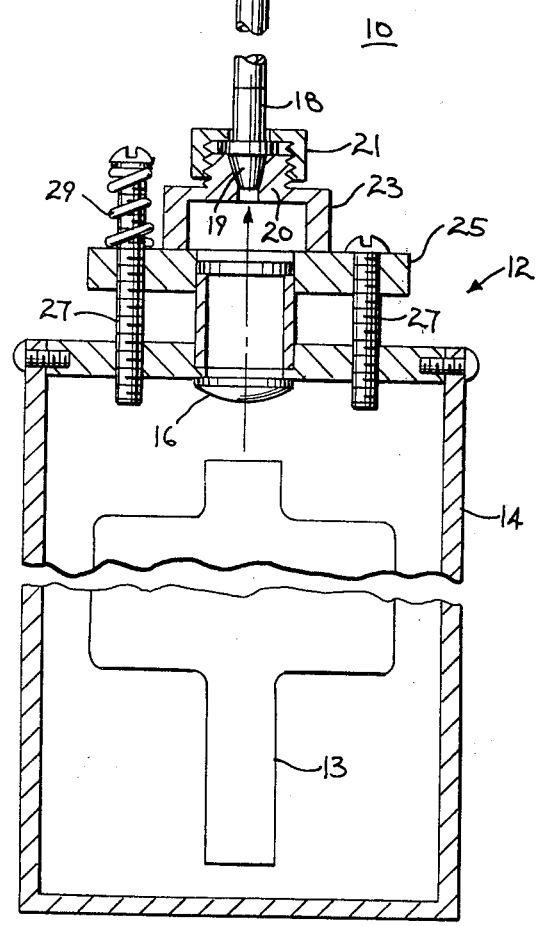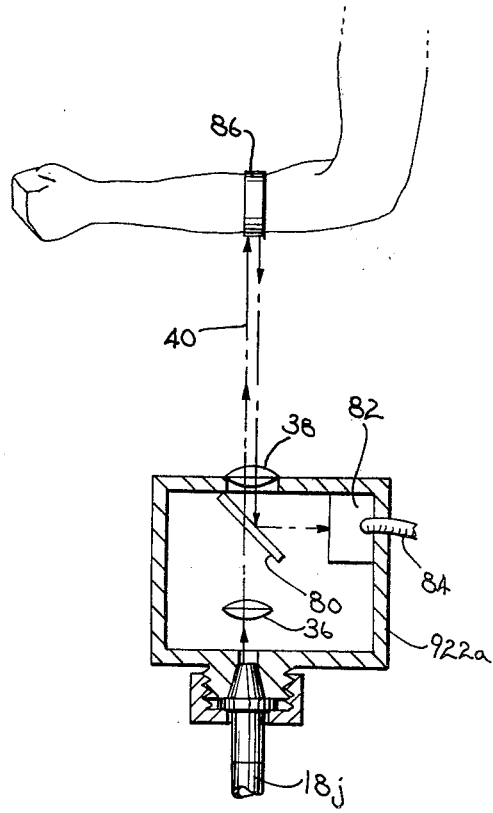
FIG.1
FIG.5

LIGHT BEAM PRODUCING DEVICE

The present invention relates to a device for producing light of desired configuration for locating and other purposes.

It is known to orient an object by means of beams of light. For example, a light source may form the beams into planes which are applied to the object to locate the object with respect to the light source. Such a technique is used to position a patient with respect to radiological equipment.

At the present time, such apparatus utilizes a separate light source for each plane or group of planes. This adds to the size, weight, complexity, cost, and power consumption of the apparatus.

In order to insure accurate positioning it is desirable that the beams of light be highly stable. However, in the past instabilities in the light source have occurred due to ambient conditions, shock, aging, or conditions in the light source itself, such as movement of a lamp filament when heated. These instabilities detract from the sought-for precision in positioning.

Radiological equipment of the axial tomographic type produces an image along a plane parallel to the X-ray beam rather than normal to it as in conventional radiography. For this purpose, the X-ray generator and detector, mounted in diametrically opposed positions, rotate in a donut shaped gantry. The portion of the patient to be examined is inserted in the central hole.

In order to enhance the usefulness of tomographic equipment as a diagnostic tool, it is desirable to position the patient as accurately as possible with respect to the X-ray elements to insure the image is obtained in the desired plane. However, accurate positioning has been hampered in the past because the patient must be moved and located in the central hole in order to make the exposure. In accordance with past practice, positioning has generally been carried out by aligning the patient outside the machine as by the planes of light noted above, or other techniques. However, the possibility of the patient shifting after alignment, during transport and exposure is ever present, substantially reducing the certainty of proper positioning.

While it would be preferably to mount the alignment means directly along the imaging plane of the tomographic equipment, this has heretofore been difficult or impossible due to the small spaces or clearances available in the equipment and the possibility of interference with the X-ray beam.

It is, therefore, the object of the present invention to provide an improved light source device suitable for orienting and other purposes. The device is simple in construction, economical and highly stable in operation, and versatile in application. Among other uses, the device may be utilized in conjunction with tomographic equipment to provide an indication on the patient of the exact plane along which the tomographic image will be taken. The device may also provide an indication that the patient is in a desired location as well as any subsequent deviation therefrom.

Briefly, the present invention contemplates a device incorporating a light source, preferably of the laser type. The device includes means for concentrating the light from the source and an elongated, solid, light conducting means, such as a fiber optic system, for conducting the concentrated light to one or more locations remote from the source. Lens or other means receive the light from the transmitting means and form it into beams of the desired configuration, such as planes.

When used as an orienting means, the planes of light of the device are applied to the object for orientation. The device may be used in conjunction with retroreflective means to include apparatus for receiving light reflected back along the beam and for providing a signal responsive thereto, indicative of the desired orientation of the object.

The device finds use in tomographic imaging apparatus for defining the imaging plane. For this purpose, a plurality of light beam forming means may be positioned on the gantry or frame of the tomographic apparatus.

The device of the present invention achieves simplicity and economy through the use of a single light source for a plurality of remotely located light beam forming means. It achieves versatility in that the small size of the light beam forming means permits their positioning at locations that have heretofore been inaccessible. Use of a laser light source provides both high light power and a high degree of stability. Use of fiber optic conductors permits high light power to be transmitted in the device.

The device of the present invention will be further understood by reference to the following drawings.

FIG. 1 is a cross sectional view showing the improved light beam producing device of the present invention.

FIG. 5 is a diagrammatic perspective view of a modified embodiment of the light beam producing device of the present invention incorporating means responsive to reflected light.

Figure 2:
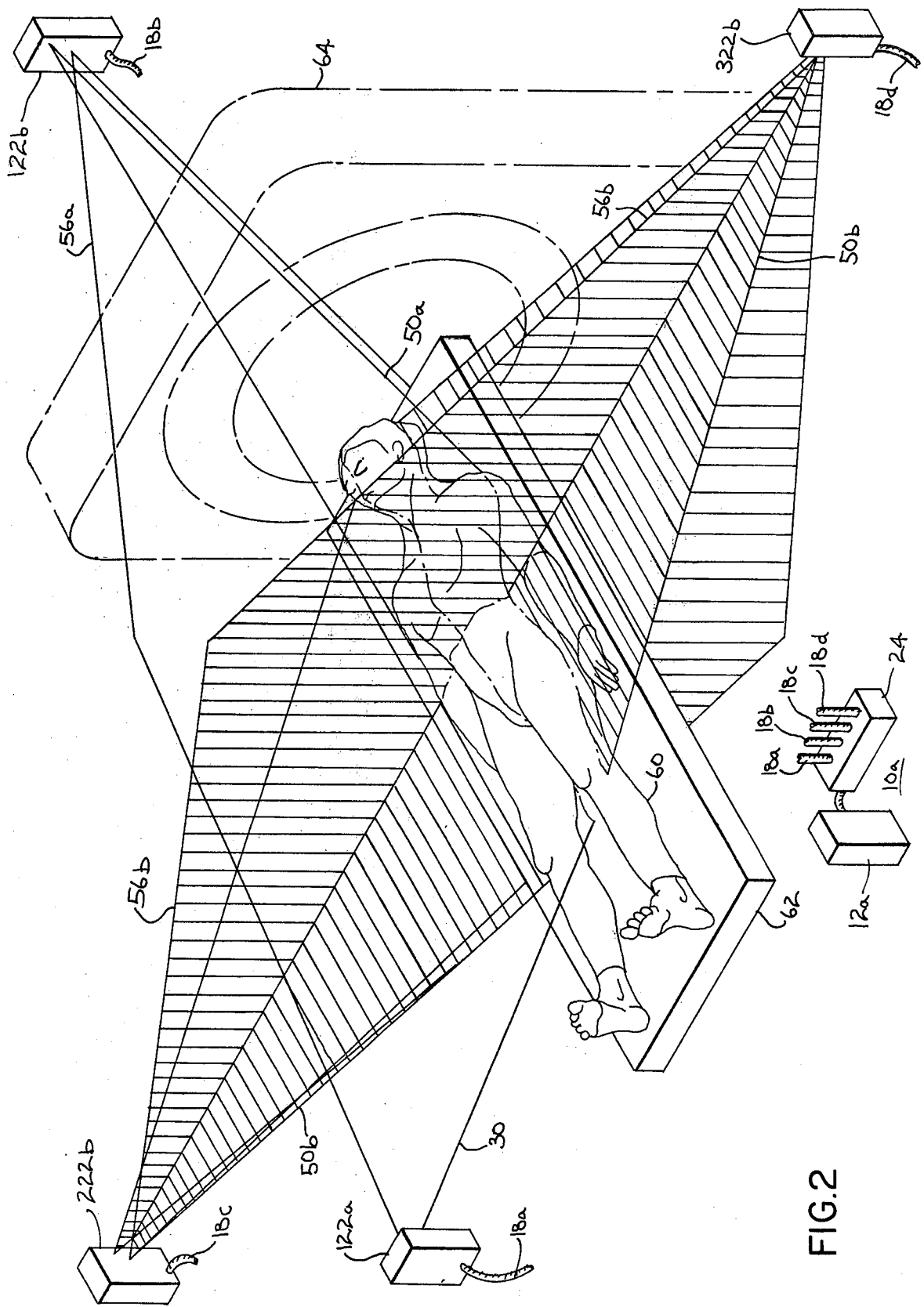
FIG. 2 is a diagrammatic perspective view of the use of the light beam producing device shown in FIG. 1 in orienting a patient.

The details of light beam producing device 10 are shown in FIG. 1. Light beam producing device 10 includes light source 12 mounted in cabinet 14. Light source 12 preferably includes laser 13 because of its high stability due to the absence of a filament and for other reasons. However, it will be appreciated that other types of radiant energy, such as infrared or other types of sources, such as incandescent, may be used in device 10 and it is intended to include in the claims all such suitable types and sources of radiant energy as may be used in device 10.

The light emitted by laser 13 is passed through converging lens 16 which concentrates the light emerging from laser 13 into a small area. The end of fiber optic conductor 18 is positioned adjacent the focal point of lens 16. Fiber optic conductor 18 terminates in male connector 19 which fits into female connector 20 and is retained by collar 21. Female connector 20 is mounted on ring 23 positioned on flange 25. A plurality of circumferentially spaced adjustment screws 27 are positioned about the periphery of flange 25 to center fiber optic conductor 18 on lens 16. Spring 29 biases flange 25 so as to position fiber optic conductor 18 with respect to the focal point of the lens. Lens 16 and fiber optic conductor 18 may be axially adjustable with respect to each other to focus lens 16.

Fiber optic conductor 18 conveys the light from laser 13 to remotely located light beam forming means. In the embodiment shown in FIG. 1 two such light beam forming means, 22a and 22b, are shown.

To supply two light beam forming means, a splitter box 24 connected to fiber optic conductor 18 may be used. Splitter box 24 contains half silvered mirror 26 to receive the light from fiber optic conductor 18. The reflected light from half-silvered mirror 26 passes through lens 28 that focuses the light on the end of fiber optic conductor 18a. The light transmitted through lens 28 passes through lens 30 that focuses the light on the end of fiber optic conductor 18b.

Light beam forming means 22a coupled to fiber optic conductor 18a includes housing 32 into which fiber optic bundle 18a projects. Fiber optic conductor 18a is positioned at the focal point of a lens 34 which forms the light emerging from the fiber optic conductor into a parallel or other desired ray configuration. Lens 34 may be moved by screw 36 relative to fiber optic conductor 18a for this purpose. The rays of light from lens 34 are applied to anamorphic lens or line generator 38 that forms the beam of light into diverging rays that lie in a vertical plane 40. While anamorphic lens 38 is specifically referred to herein, it will be appreciated that other types of line generators, such as an aperture may be used.

The construction of light beam forming means 22b is similar to that of light beam forming means 22a. The light emitted from fiber optic conductor 18b in housing 42 passes through lens 44. The light passing through lens 44 strikes half-silvered mirror 46. The reflected light from half-silvered mirror 46 travels through anamorphic lens or line generator 48 which forms the beam of light into diverging rays that lie in horizontal plane 50, shown somewhat diagrammatically in FIG. 1. The light passing through half-silvered mirror 46 strikes mirror 52. From mirror 52 the light travels through a second anamorphic lens 54 to provide vertical light plane 56.

Light beam producing device 10 thus utilizes a single light source 12 to supply a plurality of remote light beam forming means 22a and 22b lending economy to its construction and operation. The small size of light beam forming means 22a and 22b lends versatility to the application of light beam producing device 10.

While light beam forming means 22a and 22b have been described as forming planes of light, it is also possible to form other configurations such as spots. Lenses 34 and 42 are focused so that the beam emitted from the lens has approximately parallel rays, thus avoiding any depth of field problems in the use of such spots.

FIG. 2 shows the use of a plurality of light beam forming means in orienting an object, specifically, patient 60. Patient 60 is lying on table 62 for orientation with respect to radiological apparatus, such as tomographic imaging equipment 64 shown in phantom in the figure. Four light beam forming means are utilized in the exemplary embodiment of light beam producing devices 10a shown in FIG. 2. Each of the light beam forming means is connected to a common light source 12a by means of a fiber optic conductor, for example fiber optic conductor 18a through 18d extending from splitter box 24. Light beam generating means 122a may be similar to light 22a shown in FIG. 1 in that it generates a single vertical plane of light 30. Light beam generating means 122a is mounted on the wall of the room containing radiological equipment 64 so that light plane 30 has a predetermined orientation. With respect to patient 60 lying on table 62, light plane 30 forms a reference plane corresponding to the sagittal plane of the body: that is, a vertical plane running from the head to the foot of the body from the chest through the back of the body. For this purpose, light beam forming means 122a may be positioned at the foot of patient 60.

A second light beam forming means 122b is positioned on the wall at the opposite end of the sagittal plane from light beam forming means 122a. Light beam forming means 122b may resemble light beam forming means 22b of FIG. 1 in that it provides two mutually perpendicular planes of light 50a and 56a. Light plane 56a forms the other end of the sagittal plane. Light plane 50a forms the frontal reference plane; that is, a horizontal plane, when patient 60 is lying on table 62, taken from one side of the body through to the other.

Additional light beam forming 222b and 322b, similar to light beam forming means 22b of FIG. 1, may be positioned in the room so that light planes 56b and 50b perpendicularly intersect light planes 30 and 56a. The light planes 56b from light beam forming means 222b and 322b complete the frontal plane. Light planes 50b form the transverse reference plane of the body; that is, a vertical plane, with patient 60 lying on table 62, taken from side to side across the body.

In use, light source 12 is energized to provide light planes 30, 50a, 56a, 50b and 56b from light beam forming means 122a, 122b, 222b and 322b. As shown in FIG. 2, this establishes a set of orthogonal reference planes corresponding to the sagittal, frontal and transverse anatomic planes of the body.

Patient 60 reclines on table 62 so that the light planes are applied to his/her body. The intersection of the light planes with the body forms luminous lines, as shown in FIG. 2, on the patient 60. The position of the patient is altered so that the patient is properly oriented with respect to the light planes. For example, patient 60 may be positioned so that light planes 30 and 56a run up the center of the body. The patient is similarly oriented in a desired manner with respect to the planes forming the frontal and transverse reference planes. When the orientation is complete, the patient may be moved into the path of the radiation beam of equipment 64 and exposed to the necessary diagnostic or therapeutic radiation.

While the light beam producing device 10a provides accurate orientation of patient 60, it will be appreciated that the orientation with respect to planes 56b and 50b will be lost as patient 60 moves into tomographic imaging apparatus 64. Further, no indication of the imaging plane of apparatus 64 is provided by light beam producing device 10a. Light beam producing device 10b shown in FIG. 3 obviates these shortcomings. Tomographic imaging apparatus 64 includes frame 66 containing gantry 68. X-ray generator 70 and diametrically opposite detector array 72 are mounted for rotation in gantry 68. The X-ray beam passes through slit 74 as the generator and detector rotate so that the image will be formed along the plane of slit 74.

Light beam forming means 222a and 322a similar in construction to light beam forming means 22a of FIG. 1, are positioned in frame 66 so that light beams 30a and 30b project through slit 74 in the plane of the X-ray image. The light beam forming means are supplied with light from light source 12b and splitter 24 through fiber optic conductors 18e and 18f. The orientation of patient 60 with respect to this plane can thus be easily and accurately ascertained. Light beam forming means 222a and 322a may be positioned in frame 66 so as to minimize the blocking of light beams 30a and 30b as X-ray generator 70 and detector 72 rotate. The small size of light beam forming means 222a and 322a permits their positioning withing the cramped confines of tomographic imaging apparatus 64.

Figure 4:
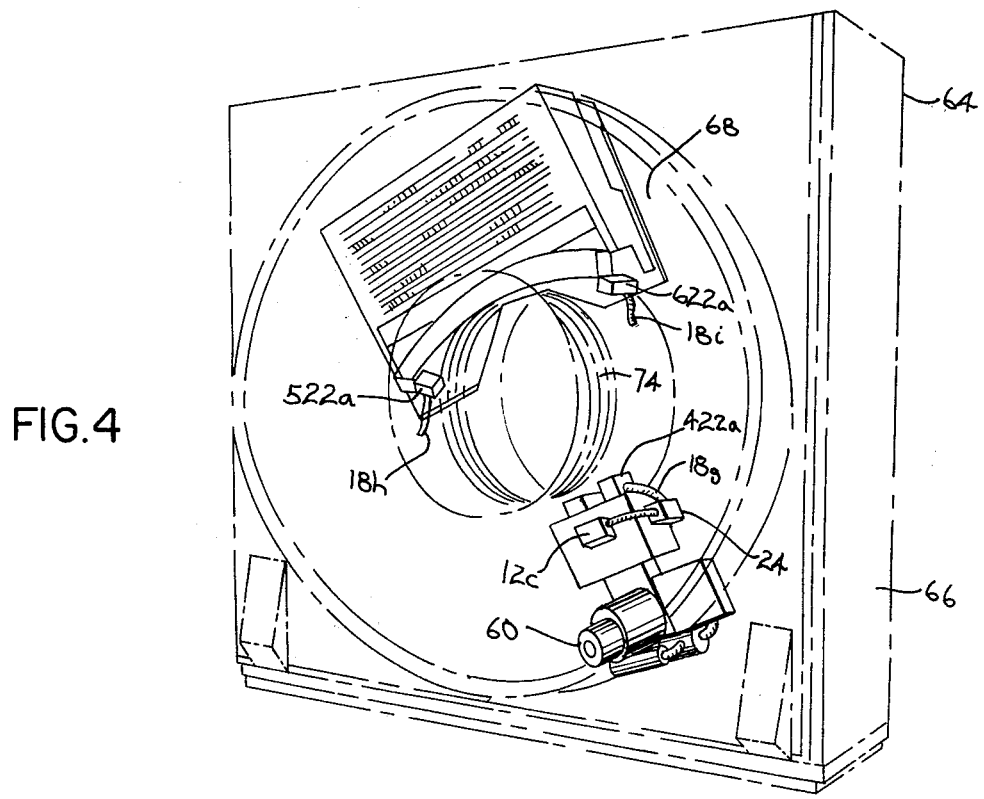
FIG. 4 is a perspective view of axial tomographic equipment incorporating the light beam producing device of the present invention in a different configuration.

If it is desired to reduce or eliminate blockage of the light beams by the X-ray equipment, the light beam forming means may be mounted on the X-ray equipment itself, as shown in FIG. 4. Light source 12c and splitter 24 may, for example, be mounted on X-ray generator 70 and connected to light beam forming means 422a, also mounted on X-ray generator 60 and light beam forming means 522a and 622a mounted on detector 72, by fiber optic conductors 18g, 18h, and 18i. Light beam forming means 422a, 522a, and 622a rotate with X-ray generator 70 and detector 72 to provide a continuous indication of the imaging plane.

Figure 3:
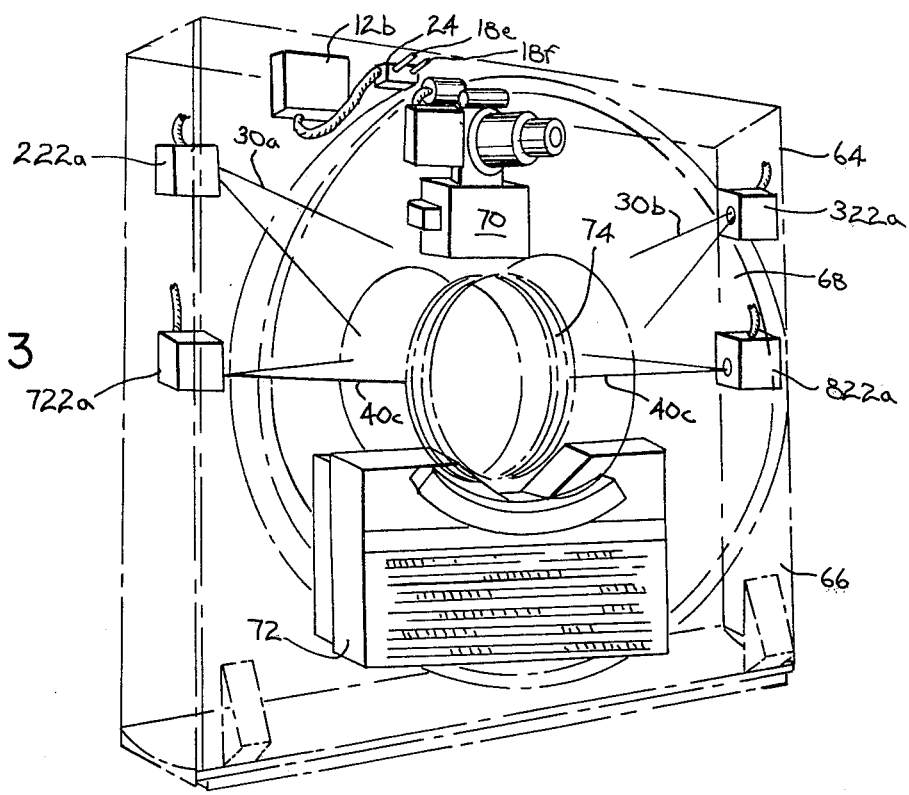
FIG. 3 is a perspective view of axial tomographic equipment incorporating the light beam producing device of the present invention of one configuration.

If desired, other planes beside the imaging plane may be indicated through slit 74. For example, as shown in FIG. 3, light beam forming means 722a and 822a may be mounted on frame 66 to form a horizontal plane of light 40c parallel to table 62 and the frontal plane of patient 60. Light beam forming means 722a and 822a may be supplied with light from source 12b through fiber optic conductors.

In some instances, it may be desirable to provide a control signal indicative of the positioning of the object with respect to the light beam forming means. This signal may be used to indicate the position of the object as correct or incorrect and to control apparatus, such as tomographic imaging apparatus 64 so as to permit operation of the equipment only when patient 60 is properly positioned along the imaging plane. FIG. 5 shows such an apparatus.

Light beam forming means 922a is constructed in a manner similar to light beam forming means 22a to include fiber optic conductor 18j, lens 36, and anamorphic lens 38 forming light plane 40. A half-silvered mirror 80, set at an angle to light plane 40 is interposed between lens 36 and lens 38.

Light reflected back along plane 40 is caught by two way mirror 80 and reflected onto photoelectric element 82. Photoelectric element 82 provides an electrical signal in conductor 84 when light is applied to it.

A reflective target 86 is placed on the skin of patient 60 along the desired plane of orientation. This target is typically a spot or narrow strip of tape of the retroreflective type which reflects incident light falling thereon back along the axis of the incident light. The photoelectric scanning tape manufactured and sold by the 3M Co., St. Paul, Minn., as stock No. 7900 is suitable for this purpose. When patient 60 is properly positioned with respect to light plane 40, the light plane will be applied to retroreflective tape 86. This will cause light to be reflected back along plane 40 to two way mirror 80, where it is reflected to photosensitive element 82 to provide an electrical signal in conductor 84. This electrical signal indicates that patient 60 is properly positioned with respect to light plane 40. If patient 60 is improperly positioned, no such signal will appear in conductor 84. Conductor 84 may be connected to apparatus, such as tomographic imaging apparatus 64, to prevent operation of the apparatus except when patient 60 is properly positioned.

Various modes in carrying out the invention are contemplated as being within the scope of the following claims, particularly pointing out and distinctly claiming the subject matter which is regarded as the invention.

We claim:

1. An object orienting device for producing at least one beam of light having a desired configuration and forming a reference datum for the object at an orientation location, said device comprising:
   a source of light positioned at one location;
   means for concentrating the light from said source;
   elongated, solid light transmitting means for receiving and transmitting the concentrated light to the orientation location that is remote from said first location; and
   lens means positioned at the orientation location for receiving the light from said transmitting means, said lens means forming the light into a beam of the desired configuration and projecting same as a reference datum at the orientation location.

2. The device according to claim 1 wherein said lens means is further defined as forming said light into a projected reference datum plane.

3. The device according to claim 1 wherein said source of light comprises a laser.

4. The device according to claim 1 wherein said concentrating means comprises a lens.

5. The device according to claim 1 wherein said lens means is further defined as forming the light into a projected reference datum beam having parallel rays.

6. The device according to claim 1 wherein said lens means comprises an anamorphic lens.

7. The device according to claim 1 wherein said light transmitting means comprises a fiber optic light conducting means.

8. The device according to claim 1 wherein said lens means provides a plurality of intersecting planes of light.

9. The device according to claim 1 including a plurality of light transmitting means receiving and transmitting the concentrated light and a plurality of lens means for receiving the transmitted light and forming beams of desired configurations at the orientation location.

10. The device according to claim 9 including means interposed in said light transmitting means for coupling a single light transmitting means receiving the concentrated light to a plurality of light transmitting means having associated lens means.

11. The device according to claim 1 wherein said device has means for receiving light reflected back along the beam of light and for providing a signal responsive thereto.

12. The device according to claim 1 wherein the object is a patient and wherein the device is further defined as one for positioning the patient with respect to radiological apparatus.

13. The device according to claim 12 wherein said device is further defined as mountable on a tomographic radiographic imaging apparatus for defining the imaging plane.

14. The device according to claim 13 including a plurality of light transmitting means and lens means mountable on said tomographic imaging apparatus for defining the imaging plane.

15. The device according to claim 13 wherein the tomographic imaging apparatus has movable radiographic elements mounted in a frame and wherein said lens means is mountable on the frame.

16. The device according to claim 13 wherein said device is further defined as mountable on the tomographic imaging apparatus for further defining a plane normal to the imaging plane.

17. The device according to claim 13 wherein the tomographic imaging apparatus has movable radiographic elements and wherein said lens means is mounted on the movable radiographic elements.

18. The device according to claim 17 wherein the tomographic imaging apparatus has a stationary frame supporting the movable elements and wherein additional lens means are mounted on the frame.

* * * * *